United States Patent [19]

Cabardo, Jr.

[11] 4,276,287

[45] Jun. 30, 1981

[54] PERIODONTAL POWDER

[76] Inventor: Alberto Cabardo, Jr., 709 Timberland Dr., Berrien Springs, Mich. 49103

[21] Appl. No.: 848,802

[22] Filed: Nov. 7, 1977

Related U.S. Application Data

[63] Continuation of Ser. No. 681,618, Apr. 29, 1976, abandoned, which is a continuation-in-part of Ser. No. 256,388, May 24, 1972, abandoned.

[51] Int. Cl.³ .............. A61K 33/06; A61K 7/16; A61K 33/00; A61K 7/24
[52] U.S. Cl. ................................. 424/154; 424/49; 424/55; 424/58; 424/127; 424/195; 424/270
[58] Field of Search ................................. 424/49–58, 424/27, 154, 195, 270

[56] References Cited

PUBLICATIONS

Principles & Practice of Modern Cosmetics 2 23 (1963), Chemical Publishing Co., Inc., N.Y.
Accepted Dental Remedies, 32nd Ed, pp. 156, 175 and 177 (1967), American Dental Associaton.
Accepted Dental Therapeutics, 33rd Ed, pp. 185–186 (1969–1970), American Dental Assoc.
Accepted Dental Therapeutics, 34th Ed, pp. 199–200 and 253 (1971–1972), American Dental Assoc.

*Primary Examiner*—Douglas W. Robinson
*Attorney, Agent, or Firm*—Lockwood, Dewey, Alex & Cummings

[57] ABSTRACT

A periodontal powder comprising approximately 288 grams of evenly exsiccated potassium alum powder and approximately 144 grams of sodium bicarbonate powder. Flavoring, sweetening, coloring, scenting and antiseptic ingredients are added.

16 Claims, 4 Drawing Figures

POWDER: EVENLY EXSICCATED POTASSIUM ALUM.——288 GM.
SODIUM BICARBONATE————144 GM.
SODIUM SACCHARIN, N., F.————1.2 GM.

LIQUID: METHYL SALICYLATE, U.S.P.————5 CC.
EUCALYPTUS OIL, U.S.P.————6 CC.
ANISE OIL, U.S.P.————5 CC.
OIL OF PEPPERMINT, U.S.P.————6 CC.
CERTIFIED FOOD COLOR————5 gtts.

MIX POTASSIUM ALUM. AND SODIUM BICARBONATE. ADD METHYL SALICYLATE, ADD EUCALYPTUS OIL. MIX SACCHARIN WITH 5 DROPS OF CERTIFIED FOOD COLOR AND ADD TO THIS, ONE TBSP. OF ABOVE MIXTURE. BLEND WITH REMAINING MIXTURE ADD ANISE OIL, AND THEN ADD OIL OF PEPPERMINT

FIG. 1.

50 GM BY WEIGHT BEFORE EXSICCATION AT 350 DEGREES F ONE HOUR EXPOSURE.

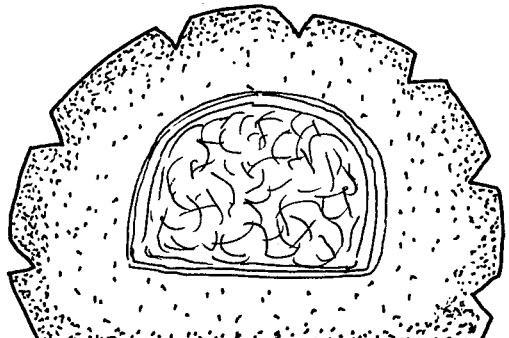

UNEVENLY EXSICCATED
FIG. 2.

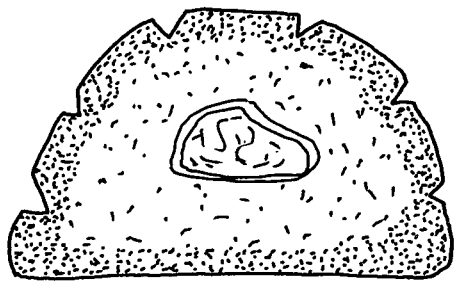

UNEVENLY EXSICCATED
FIG. 3.

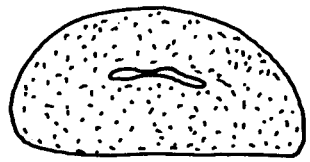

10 GM BY WEIGHT BEFORE EXSICCATION AT 350 F EXPOSURE 1 HOUR EVENLY EXSICCATED

FIG. 4.

PERIODONTAL POWDER

This is a continuation of application Ser. No. 681,618, filed Apr. 29, 1976, now abandoned, which latter application is a continuation-in-part application of Ser. No. 256,388, filed May 24, 1972, now abandoned.

DESCRIPTION OF THE INVENTION:

The present invention relates a periodontal powder and a method of making same.

The principal object of the invention is to provide a method of making a periodontal powder which is simple in execution.

An object of the invention is to provide a periodontal powder which is a potent aid to periodontal therapy, controls simple gum bleeding and is a considerable aid in the treatment of chronic and acute gingivitis.

In order that the invention may be readily carried into effect, it will now be described with reference to the accompanying drawing, wherein:

FIG. 1 is a flow chart of the method of making the composition the invention;

FIG. 2 is a cross-sectional view of unevenly exsiccated potassium alum powder;

FIG. 3 is a cross-sectional view of unevenly exsiccated potassium alum powder; and FIG. 4 is a cross-sectional view of evenly exsiccated potassium alum powder.

The method of making the periodontal powder in accordance with the invention comprises the steps of mixing 288 grams of evenly exsiccated potassium alum powder with 144 grams of sodium bicarbonate powder. 5 cc of liquid methyl salicylate is added. 6 cc of eucalyptus oil is added.

Five drops of certified food color is mixed with 1.2 grams of sodium saccharin powder. The sodium saccharin and food color are added to one tablespoonful of the potassium alum, sodium bicarbonate, methyl salicylate, eucalyptus oil mixture to provide a sub-mixture. The sub-mixture is blended with the remaining mixture of potassium alum, sodium bicarbonate, methyl salicylate and eucalyptus oil.

5 cc of anise oil is added to the resultant mixture. 6 cc of oil of peppermint is added to the mixture.

The principal chemical agent is the evenly exsiccated potassium alum powder. The base chemical is sodium bicarbonate. Eucalyptus oil and methyl salicylate are included for their antiseptic property. Oil of peppermint and anise oil are utilized to provide flavoring. Saccharin is added for sweetening. Food coloring is provided for attractive coloring.

The mixing throughout the process is thorough and well executed. The mixture at each stage is even and smooth.

The resultant mixture is permitted to stand one half to one hour, or a little longer, before the periodontal powder is packed and permanently sealed. This eliminates or minimizes pressure within the container.

The periodontal powder is useful as tooth powder in brushing the teeth and massaging the gums. For simple bleeding of gums and/or swollen gums, the periodontal powder is dissolved in enough water to make a paste. A cotton swab is utilized to apply the paste to tender, swollen or bleeding areas by pressing gently, but firmly against the gum tissue. This should be done two or three times daily.

While the invention has been described by means of specific examples and in specific embodiments, I do not wish to be limited thereto, for obvious modifications will occur to those skilled in the art without departing from the spirit and scope of the invention.

I claim:

1. A method of periodontal therapy for bleeding and swollen gums and gingivitis comprising the step of applying a therapeutically effective amount topically to the gums of a mixture of evenly exsiccated potassium alum and sodium bicarbonate in a ratio, by weight, of approximately 2:1 of said potassium alum to said sodium bicarbonate.

2. The method of claim 1, wherein said mixture further includes at least one antiseptic agent.

3. The method of claim 2, wherein said antiseptic agent is selected from the group consisting of methyl salicylate, eucalyptus oil and mixtures thereof.

4. The method of claim 1 wherein said mixture includes at least one flavoring agent.

5. The method of claim 4 wherein said flavoring agent includes a material selected from the group consisting of oil of peppermint, anise oil and mixtures thereof.

6. The method of claim 1 wherein said mixture further includes at least one sweetening agent.

7. The method of claim 6 wherein said sweetening agent is saccharin.

8. The method of claim 1 wherein said mixture includes a coloring agent.

9. The method of claim 8 wherein said coloring agent is a food coloring.

10. The method of claim 1 wherein said mixture further includes at least one antiseptic agent, at least one flavoring agent, at least one sweetening agent and at least one coloring agent.

11. The method of claim 10 wherein said antiseptic agent is selected from the group consisting of methyl salicylate, eucalyptus oil and mixtures thereof, said flavoring agent is selected from the group consisting of oil of peppermint, anise oil and mixtures thereof, said sweetening agent is saccharin, and said coloring agent is a food color.

12. The method of claim 1 wherein said mixture comprises materials in proportion to the following:
   approximately 288 grams of said finely exsiccated potassium alum;
   approximately 144 grams of said sodium bicarbonate;
   approximately 5 cc of methyl salicylate;
   approximately 6 cc of eucalyptus oil;
   approximately 1.2 grams of sodium saccharin;
   approximately 5 drops of certified food color;
   approximately 5 cc of anise oil; and
   approximately 6 cc of oil of peppermint.

13. The method of claim 1 wherein said mixture is mixed with an amount of liquid sufficient to form a paste, said paste being applied topically to said gums.

14. The method of claim 2 wherein said last mentioned mixture is mixed with an amount of liquid sufficient to form a paste, said paste being applied topically to said gums.

15. The method of claim 10 wherein said last mentioned mixture is mixed with an amount of liquid sufficient to form a paste, said paste being applied topically to said gums.

16. The method of claim 12 wherein said mixture of materials is mixed with an amount of liquid sufficient to form a paste, said paste being applied topically to said gums.

* * * * *